US006277832B1

(12) United States Patent
Sugiyama et al.

(10) Patent No.: US 6,277,832 B1
(45) Date of Patent: Aug. 21, 2001

(54) GROWTH INHIBITOR FOR LEUKEMIA CELLS COMPRISING ANTISENSE OLIGONUCLEOTIDE DERIVATIVE TO WILMS TUMOR GENE (WT1)

(75) Inventors: Haruo Sugiyama, Mino; Tamotsu Yamagami, Takatsuki; Kazushi Inoue, Ibaraki, all of (JP)

(73) Assignee: Tadamitsu Kishimoto, Tondabayashi (JP)

( * ) Notice: Subject to any disclaimer, the term of this patent is extended or adjusted under 35 U.S.C. 154(b) by 0 days.

(21) Appl. No.: 09/487,874

(22) Filed: Jan. 20, 2000

Related U.S. Application Data

(62) Division of application No. 08/952,664, filed as application No. PCT/JP96/01394 on May 24, 1996, now Pat. No. 6,034,235.

(30) Foreign Application Priority Data

Jun. 1, 1995 (JP) ................................................... 7-156672

(51) Int. Cl.$^7$ .......................... A61K 48/00; C07H 21/04; C12N 15/85
(52) U.S. Cl. ................................ 514/44; 435/6; 435/325; 435/366; 435/375; 536/24.5
(58) Field of Search .................................. 514/44; 435/6, 435/325, 366, 375; 536/24.5

(56) References Cited

PUBLICATIONS

Branch, A good antisense molecule is hard to fine, TIBS, vol. 23, pp. 45–50, Feb. 1998.*
Agrawal, Antisense oligonucleotides:towards clinical trials, TIBTECH, vol. 14, pp. 376–387, Oct. 1996.*
Gerwirtz et al., Facilitating oligonucleotide delivery: helping antisense deliver on its promise, PNAS, vol. 93, pp. 3161–3163, Apr. 1996.*
Katherine M. Call, et al., "Isolation and Characterization of a Zinc Finger Polypeptide Gene at the Human Chromosome 11 Wilms' Tumor Locus", Cell, vol. 60, pp. 509–520, 02/1990.
C.E. Campbell, et al., "Antisense transcripts and protein binding motifs within the Wilms tumor (WT1) locus", Oncongene, vol. 9, pp. 583–595, 1994.
Daniel A. Haber, et al., "Alternative splicing and genomic structure of the Wilms tumor gene WT1", Proc. Nat'l. Acad. Sci, USA, vol. 88, pp. 9618–9622, 11/1991.
Tom Atkinson, et al., "Solid–phase Synthesis of Oligodeoxyribo–nucleotides by the Phosphite–triester Method", pp. 35–81, 1985.
Marvin H. Caruthers, "Gene Synthesis Machines: DNA Chemistry and Its Uses", Science, vol. 230, pp. 281–285, 10/1985.

Akiko Kume, et al., "Acylphosphonates. 4.$^1$ Synthesis of Dithymidine Phosphonate: A New Method for Generation of Phosphonate Function via Aroylphosphonate Intermediates", J. Org. Chem., vol. 49, pp. 2139–2143, 1984.
B.C. Froehler, et al., "Nucleoside H–Phosphonates: Valuable Intermediates in the Synthesis of Deoxyoligonucleotides", Tetrahedron Letters, vol. 27, No. 4, pp. 469–472, 1986.
Per J. Garegg, et al., "Nucleoside H–Phophonates. III. Chemical Synthesis of Oligodeoxyribonnucleotides by the Hydrogenphosphonate Approach", Tetrahedron Letters, vol. 27, No. 34, pp. 4051–4054, 1986.
Brian S. Sproat, et al., "Solid–phase Synthesis of Oligodeoxyribonucleotides by the Phosphotriester Method", Oligonucleotide synthesis: a practical approach, pp. 83–113, 1984.
S. L. Beaucage, et al., Deoxynucleoside Phosphoramidites–A New Class of Key Intermediates for Deoxypolynucleotide Synthesis, Tetrahedron Letters, vol. 22, No. 22, pp. 1859–1862, 1981.
C. L. Hulse, et al., "Evidence for a Copper–Nitrosyl Intermediate in Denitrification by the Copper–Containing Nitrite Reductase of Achromobacter cycloclastes", J. Am., Chem. Soc. vol. 111, pp. 2322–2323, 1989.
M. D. Matteucci, et al., "The Synthesis of Oligodeoxypyrimidines On Polymer Support", Tetrahedron Letters, vol. 21, pp. 719–722, 1980
M. D. Matteucci, et al., "Synthesis of Deoxylignucleotides on a Polymer Support$^1$", J. Am. Chem. Soc., vol. 103, pp. 3185–3191, 1981.
Harold M. Moody, et al., "Regiospecific inhibition of DNA duplication by antisense phosphate–methylated oligodeoxynucleotides", Nucleic Acids Research, vol. 17, No. 12, pp. 4769–4782, 1989.
M.A. Dorman, et al., "Synthesis of Oligodeoxynucleotides and Oligodeoxynucleotide Analogs Using Phosphoramidite Intermediates", Tetrahedron, vol. 40, No. 1, pp. 95–102, 1984.
C.A. Stein, et al., "Physicochemical properties of phosphorothioate oligodeoxynucleotides", Nucleic Acids Research, vol. 16, No. 8, pp. 3209–3221, 1988.
Huynh Vu, et al., "Internucleotide Phosphite Sulfurization with Tetraethylthiuram Disulfide Phosphorothioate Oligonucleotide Synthesis Via Phosphoramidite Chemistry", Tetrahedron Letters, vol. 32, No. 26, pp. 3005–3008, 1991.

(List continued on next page.)

Primary Examiner—Andrew Wang
(74) Attorney, Agent, or Firm—Foley & Lardner

(57) ABSTRACT

This invention provides a growth inhibitor for leukemia cells comprising an antisense oligonucleotide derivative to Wilms' tumor gene (WT1).

4 Claims, 8 Drawing Sheets

OTHER PUBLICATIONS

B. Froehler, et al., "Phosphoramidae analogues of DNA: synthesis and thermal stability of heteroduplexes", vol. 16, No. 11, pp. 4831–4839, 1988.

Hiroaki Ozaki, et al., "Synthesis, Isolation and Characterization of Diasterochemically Pure Dithymidine Phosphormorpholidate Derivatives", *Tetrahedron Letters*, vol. 30, No. 43, pp. 5899–5902, 1989.

Kan L. Agarwal, et al., "Synthesis and enzymatic properties of deoxyribooligonucleotides containing methyl and phenylphosphonate linkages", *Nucleic Acids Research*, vol. 6, No. 9, pp. 3009–3024, 1979.

Rothenpieler, Antisense oligodeoxynucleotides directed against Wilms tumor gene wt1 inhibit kidney differentiation and development, J. Am. Soc. Nephr., vol. 5 (3), pp 635.

James, Toward gene inhibition therapy: a review of progress and prospects in the field of antiviral antisense nucleic acids and ribozymes, Antiviral Chem. Chemo, vol. 2 (4), pp 191–214.

* cited by examiner

A

B

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:1:

CCCACCGCAT TCGACCCT                                                      18

(2) INFORMATION FOR SEQ ID NO:2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:2:

AGGGTCGAAT GCGGTGGG                                                      18

(2) INFORMATION FOR SEQ ID NO:3:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:3:

CCGGCCCCTC TTATTTGA                                                      18

(2) INFORMATION FOR SEQ ID NO:4:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:4:

TCAAATAAGA GGGGCCGG                                                      18

(2) INFORMATION FOR SEQ ID NO:5:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
    (A) DESCRIPTION: /desc = "Synthetic DNA"

(xi) SEQUENCE DESCRIPTION: SEQ ID NO:5:

CAGCAAATGG GCTCCGAC                                                    18

(2) INFORMATION FOR SEQ ID NO:6:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:6:

GTCGGAGCCC ATTTGCTG                                                    18

(2) INFORMATION FOR SEQ ID NO:7:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:7:

AGCGATAACC ACACAACG                                                    18

(2) INFORMATION FOR SEQ ID NO:8:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:8:

CGTTGTGTGG TTATCGCT                                                    18

(2) INFORMATION FOR SEQ ID NO:9:

(i) SEQUENCE CHARACTERISTICS:
       (A) LENGTH: 1272 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:9:

TGGTATCCTC GACCAGGGCC ACAGGCAGTG CTCGGCGGAG TGGCTCCAGG AGTTACCCGC      60

TCCCTGCCGG GCTTCGTATC CAAACCCTCC CCTTCACCCC TCCTCCCCAA ACTGGGCGCC     120

AGGATGCTCC GGCCGGAATA TACGCAGGCT TTGGGCGTTT GCCAAGGGTT TTCTTCCCTC     180

CTAAACTAGC CGCTGTTTTC CCGGCTTAAC CGTAGAAGAA TTAGATATTC CTCACTGGAA     240

AGGGAAACTA AGTGCTGCTG ACTCCAATTT TAGGTAGGCG GCAACCGCCT TCCGCCTGGC     300

-continued

```
GCAAACCTCA CCAAGTAAAC AACTACTAGC CGATCGAAAT ACGCCCGGCT TATAACTGGT      360

GCAACTCCCG GCCACCCAAC TGAGGGACGT TCGCTTTCAG TCCCGACCTC TGGAACCCAC      420

AAAGGGCCAC CTCTTTCCCC AGTGACCCCA AGATCATGGC CACTCCCCTA CCCGACAGTT      480

CTAGAGCAAG AGCCAGACTC AAGGGTGCAA AGCAAGGGTA TACGCTTCTT TGAAGCTTGA      540

CTGAGTTCTT TCTGCGCTTT CCTGAAGTTC CCGCCCTCTT GGAGCCTACC TGCCCCTCCC      600

TCCAAACCAC TCTTTTAGAT TAACAACCCC ATCTCTACTC CCACCGCATT CGACCCTGCC      660

CGGACTCACT GCTACTGAAC GGACTCTCCA GTGAGACGAG GCTCCCACAC TGGCGAAGGC      720

AAGAAGGGGA GGTGGGGGGA GGGTTGTGCC ACACCGGCCA GCTGAGAGCG CGTGTTGGGT      780

TGAAGAGGAG GGTGTCTCCG AGAGGGACGC TCCCTCGGAC CCGCCCTCAC CCCAGCTGCG      840

AGGGCGCCCC CAAGGAGCAG CGCGCGCTGC CTGGCCGGGC TTGGGCTGCT GAGTGAATGG      900

AGCGGCCGAG CCTCCTGGCT CCTCCTCTTC CCCGCGCCGC CGGCCCCTCT TATTTGAGCT      960

TTGGGAAGCT GAGGGCAGCC AGGCAGCTGG GGTAAGGAGT TCAAGGCAGC GCCCACACCC     1020

GGGGGCTCTC CGCAACCCGA CCGCCTGTCG CTCCCCCACT TCCCGCCCTC CCTCCCACCT     1080

ACTCATTCAC CCACCCACCC ACCCAGAGCC GGGACGGCAG CCCAGGCGCC CGGGCCCCGC     1140

CGTCTCCTCG CCGCGATCCT GGACTTCCTC TTGCTGCAGG ACCCGGCTTC CACGTGTGTC     1200

CCGGAGCCGG CGTCTCAGCA CACGCTCCGC TCCGGGCCTG GGTGCCTACA GCAGCCAGAG     1260

CAGCAGGGAG TC                                                        1272
```

(2) INFORMATION FOR SEQ ID NO:10:

(i) SEQUENCE CHARACTERISTICS:
        (A) LENGTH: 457 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; portion of
            exon 1 of WT1 gene"

(xi) SEQUENCE DESCRIPTION: SEQ ID NO:10:

```
TCTGAGCCTC AGCAAATGGG CTCCGACGTG CGGGACCTGA ACGCGCTGCT GCCCGCCGTC       60

CCCTCCCTGG GTGGCGGCGG CGGCTGTGCC CTGCCTGTGA GCGGCGCGGC GCAGTGGGCG      120

CCGGTGCTGG ACTTTGCGCC CCCGGGCGCT TCGGCTTACG GGTCGTTGGG CGGCCCCGCG      180

CCGCCACCGG CTCCGCCGCC ACCCCCGCCG CCGCCGCCTC ACTCCTTCAT CAAACAGGAG      240

CCGAGCTGGG GCGGCGCGGA GCCGCACGAG GAGCAGTGCC TGAGCGCCTT CACTGTCCAC      300

TTTTCCGGCC AGTTCACTGG CACAGCCGGA GCCTGTCGCT ACGGGCCCTT CGGTCCTCCT      360

CCGCCCAGCC AGGCGTCATC CGGCCAGGCC AGGATGTTTC CTAACGCGCC CTACCTGCCC      420

AGCTGCCTCG AGAGCCAGCC CGCTATTCGC AATCAGG                              457
```

(2) INFORMATION FOR SEQ ID NO:11:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; exon 2 of
            WT1 gene"

(xi) SEQUENCE DESCRIPTION: SEQ ID NO:11:

GTTACAGCAC GGTCACCTTC GACGGGACGC CCAGCTACGG TCACACGCCC TCGCACCATG      60

CGGCGCAGTT CCCCAACCAC TCATTCAAGC ATGAGGATCC CATGGGCCAG CAGGGCTCGC     120

TGG                                                                  123

(2) INFORMATION FOR SEQ ID NO:12:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Sythetic DNA; exon 3 of WT1
            gene"

(xi) SEQUENCE DESCRIPTION: SEQ ID NO:12:

GTGAGCAGCA GTACTCGGTG CCGCCCCCGG TCTATGGCTG CCACACCCCC ACCGACAGCT      60

GCACCGGCAG CCAGGCTTTG CTGCTGAGGA CGCCCTACAG CAG                      103

(2) INFORMATION FOR SEQ ID NO:13:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; exon 4 of
            WT1 gene"

(xi) SEQUENCE DESCRIPTION: SEQ ID NO:13:

TGACAATTTA TACCAAATGA CATCCCAGCT TGAATGCATG ACCTGGAATC AGATGAACTT      60

AGGAGCCACC TTAAAGGG                                                   78

(2) INFORMATION FOR SEQ ID NO:14:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; exon 5 of
            WT1 gene"

(xi) SEQUENCE DESCRIPTION: SEQ ID NO:14:

AGTTGCTGCT GGGAGCTCCA GCTCAGTGAA ATGGACAGAA GGGCAGAGCA A               51

(2) INFORMATION FOR SEQ ID NO:15:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; exon 6 of
            WT1 gene"

(xi) SEQUENCE DESCRIPTION: SEQ ID NO:15:

CCACAGCACA GGGTACGAGA GCGATAACCA CACAACGCCC ATCCTCTGCG GAGCCCAATA      60

CAGAATACAC ACGCACGGTG TCTTCAGAGG CATTCAG                            97

(2) INFORMATION FOR SEQ ID NO:16:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; exon 7 of
            WT1 gene"

(xi) SEQUENCE DESCRIPTION: SEQ ID NO:16:

GATGTGCGAC GTGTGCCTGG AGTAGCCCCG ACTCTTGTAC GGTCGGCATC TGAGACCAGT    60

GAGAAACGCC CCTTCATGTG TGCTTACCCA GGCTGCAATA AGAGATATTT TAAGCTGTCC   120

CACTTACAGA TGCACAGCAG GAAGCACACT G                                  151

(2) INFORMATION FOR SEQ ID NO:17:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; exon 8 of
            WT1 gene"

(xi) SEQUENCE DESCRIPTION: SEQ ID NO:17:

GTGAGAAACC ATACCAGTGT GACTTCAAGG ACTGTGAACG AAGGTTTTCT CGTTCAGACC    60

AGCTCAAAAG ACACCAAAGG AGACATACAG                                    90

(2) INFORMATION FOR SEQ ID NO:18:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; exon 9 of
            WT1 gene"

(xi) SEQUENCE DESCRIPTION: SEQ ID NO:18:

GTGTGAAACC ATTCCAGTGT AAAACTTGTC AGCGAAAGTT CTCCCGGTCC GACCACCTGA    60

AGACCCACAC CAGGACTCAT ACAGGTAAAA CAA                                93

(2) INFORMATION FOR SEQ ID NO:19:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA; portion of
            exon 10 of WT1 gene"

(xi) SEQUENCE DESCRIPTION: SEQ ID NO:19:

GTGAAAAGCC CTTCAGCTGT CGGTGGCCAA GTTGTCAGAA AAAGTTTGCC CGGTCAGATG    60

-continued

```
AATTAGTCCG CCATCACAAC ATGCATCAGA GAAACATGAC CAAACTCCAG CTGGCGCTTT       120

GAGGCGTCTC CCTCGGGGAC CGTTCAGTGT CCCAGGCA                              158
```

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:20:

```
AGAGAAGAAG GGAACCCC                                                    18
```

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:21:

```
GCGTGGGCAG CCTGGGAA                                                    18
```

(2) INFORMATION FOR SEQ ID NO:22:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Lys His Glu Asp Pro Met Gly Gln Gln Gly Ser Leu Gly Glu Gln Gln
1               5                   10                  15
```

US 6,277,832 B1

GROWTH INHIBITOR FOR LEUKEMIA CELLS COMPRISING ANTISENSE OLIGONUCLEOTIDE DERIVATIVE TO WILMS TUMOR GENE (WT1)

This application is a divisional of application Ser. No. 08/952,664, filed Dec. 1, 1997, now U.S. Pat. No. 6,034,235, which is a National Stage of PCT/JP96/01394, filed May 24, 1996.

TECHNICAL FIELD

The present invention relates to a growth inhibitor for leukemia cells comprising an antisense nucleotide derivative.

BACKGROUND ART

Wilms' tumor is a pediatric kidney tumor that occurs as a result of deactivation of both allele of the Wilms' tumor gene (WT1) located on chromosome 11p13 (Call, K. M., et al., Cell 60: 509, 1990). A non-coding upstream sequence of WT1 (C. E. Campbell, et al., Oncogene 9: 583–595, 1994) and a coding region that includes the intron (D. A. Haber, et al., Proc. Natl. Acad. Sci. USA, 88: 9618–9622, 1991) have previously been reported, and they are expected to be involved in the growth and differentiation of the tumor and so forth (D. A. Haber, et al., Proc. Natl. Acad. Sci. USA, 88: 9618–9622, 1991).

However, it was not known that WT1 is involved in the growth of leukemia cells, and that an antisense oligonucleotide derivative to WT1 suppresses and inhibits growth of leukemia cells.

DISCLOSURE OF THE INVENTION

Thus, the present invention provides a growth inhibitor for leukemia cells comprising an antisense nucleotide derivative to Wilms' tumor gene (WT1).

DETAILED DESCRIPTION OF THE INVENTION

Figure 1:
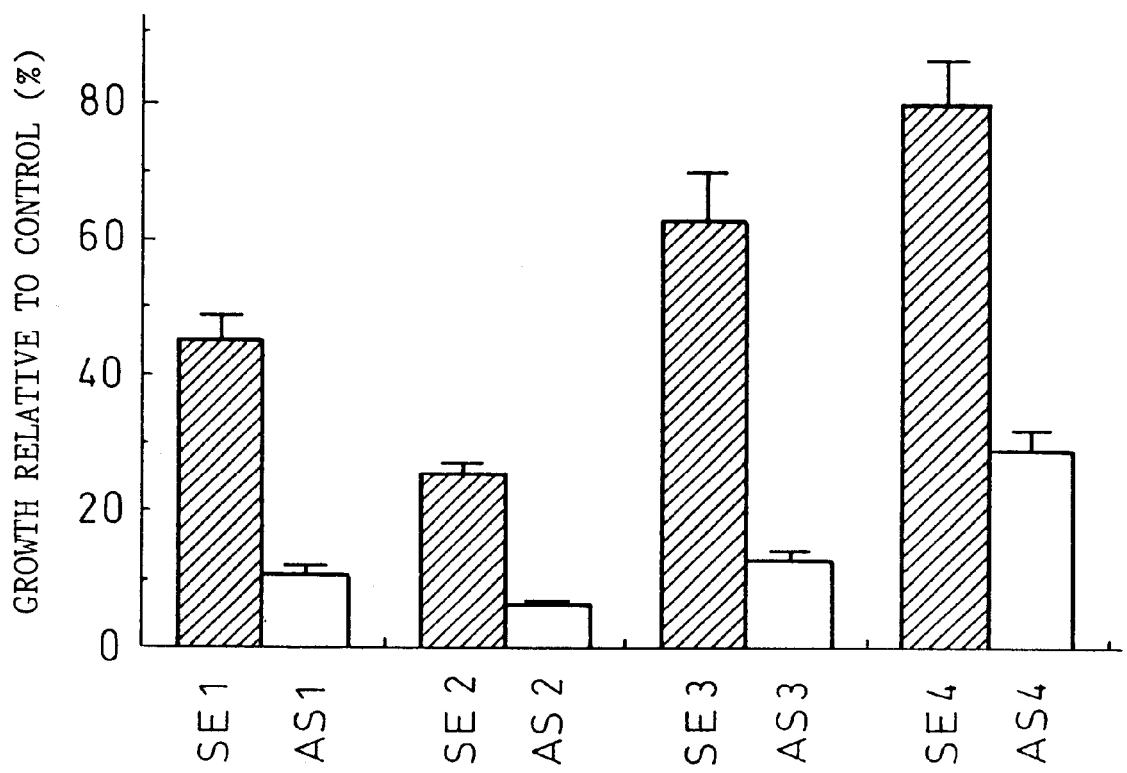
FIG. 1 is a graph showing the inhibitory effects of oligonucleotide on the growth of leukemia cell line K562.

The present invention provides a leukemia cell growth inhibitor comprising an antisense oligonucleotide derivative to WT1. The antisense oligonucleotide derivatives used in the present invention is an antisense oligonucleotide derivative to WT1, examples of which include that to the transcription capping site of WT1, gene that to the translation starting region, that to an exon or that to an intron.

For example, a nucleotide sequence of a sense DNA strand of the region containing the transcription capping site of WT1 is represented with SEQ ID NO: 9. In addition, a nucleotide sequence of a sense DNA strand of exons 1 to 10 of the region coding for WT1 is represented with SEQ ID NOS: 10 to 19. The present invention uses an antisense oligonucleotide derivative to such a nucleotide sequence of the sense DNA strand of WT1. This antisense oligonucleotide derivative is an antisense oligonucleotide derivative comprising 5 to 50 continuous nucleotides and preferably 9 to 30 nucleotides of antisense DNA or RNA chain for WT1, or 5 to 70 nucleotides and preferably 9 to 50 nucleotides intermittently or partially complementary to DNA or RNA chain for WT1 and capable of binding to DNA or RNA chain for WT1.

Examples of antisense oligonucleotide derivatives to the transcription capping site include those having the following nucleotide sequences: 5'-AGGGTCGAATGCGGTGGG-3' (SEQ ID NO: 2) and 5'-TCAAATAAGAGGGGCCGG-3' (SEQ ID NO: 4). In addition, examples of antisense oligonucleotide derivatives to the translation starting region include antisense oligonucleotide derivatives to the translation starting codon ATG and its upstream and/or downstream region such as the following nucleotide sequence: 5'-GTCGGAGCCCATTTGCTG-3' (SEQ ID NO: 6).

In addition, ten exons are contained in the region coding for WT1, and examples of the antisense oligonucleotide derivative of the present invention include those to the sequences contained in any of these exons, those to the sequences extending over any two consecutive exons after splicing or those to the sequences extending over a consecutive intron and exon, and those to sequences of all introns and the 3' and 5' non-coding regions. One example of an antisense oligonucleotide derivative is that to the 6th exon, an example of which is that to the following nucleotide sequence: 5'-CGTTGTGTGGTTATCGCT-3' (SEQ ID NO: 8).

Moreover, although there are no particular restrictions on the region corresponding to the antisense oligonucleotide derivative of the present invention having a nucleotide sequence intermittently or partially complementary to the DNA or RNA chain for WT1, those similar to ribozymes having a function to cleave the DNA chain or RNA chain for WT1 are included in these.

The structure of antisense olignucleotide derivative used in the present invention is as shown in chemical formula 1, wherein X may independently be an oxygen (O), sulfur (O), lower alkyl group, primary amine or secondary amine. Y may independently be an oxygen (O) or sulfur (S). Z is a hydrogen atom or hydroxyl group. B is chosen from adenine, guanine, thymine or cytosine when Z is a hydrogen atom, or chosen from adenine, guanine, uracil or cytosine when Z is a hydroxyl group, and is mainly an oligonucleotide complementary to DNA or mRNA coding for WT1. R is independently a hydrogen atom, dimethoxytrityl group or lower alkyl group. N is an integer of 7–28.

Chemical Formula 1

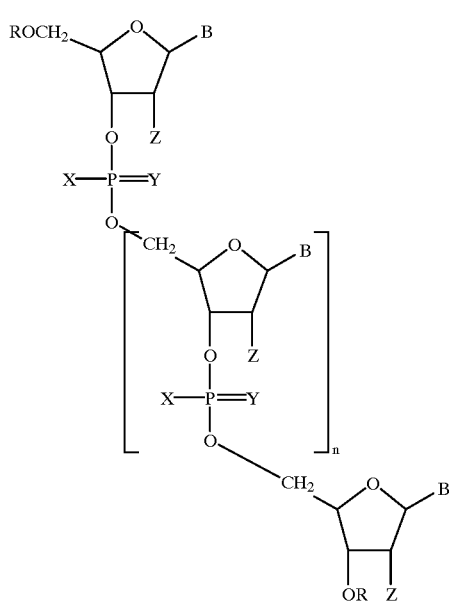

Preferable examples of antisense oligonucleotide derivatives include not only non-modified antisense oligonucleotides, but also modified antisense oligonucleotides. Examples of these modified forms include low alkyl phosphonate forms like the above-mentioned methylphosphonate form or ethylphosphonate form, and other phosphorothioate forms or phosphoroamidate forms (see chemical formula 2).

Chemical Formula 2

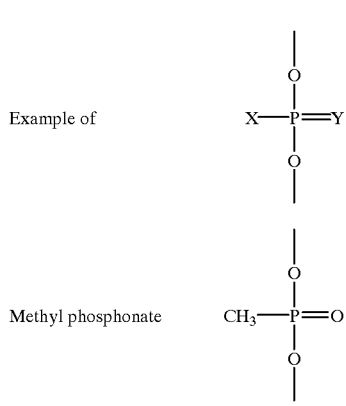

Phosphorothioate 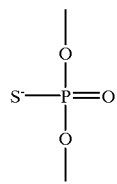

Phosphorodithioate 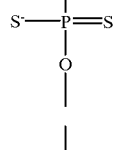

Phosphoroamidate 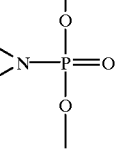

Triester phosphate 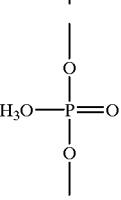

These antisense oligonucleotide derivatives can be obtained according to the following conventional methods.

The antisense oligonucleotides in which X and Y in chemical formula 1 are O and Z is a hydrogen atom or hydroxyl group are easily synthesized by a commercially available DNA synthesizer (for example, that manufactured by Applied Biosystems).

Antisense oligodeoxyribonucleotide in which Z is a hydrogen atom can be obtained by a method such as solid phase synthesis using phosphoroamidite or solid phase synthesis using hydrogen phosphonate.

See, for example, T. Atkinson and M. Smith in Oligonucleotide Synthesis: A Practical Approach, ed. M. J. Gait, IRL Press, 35–81 (1984); M. H. Caruthers, Science, 230, 281 (1985); A. Kume, M. Fujii, M. Sekine and M. Hata, J. Org. Chem., 49, 2139 (1984); B. C. Froehler and M. Matteucci, Tetrahedron Lett., 27, 469 (1986); P. J. Garegg, I. Lindh, T. Regberg, J. Stawinski, R. Stromberg and C. Henrichson, ibid., 27, 4051 (1986); B. S. Sproat and M. J. Gait in Oligonucleotide Synthesis: A Practical Approach, ed. M. J. Gait, IRL Press, 83–115 (1984); S. L. Beaucage and M. H. Caruthers, Tetrahedron Lett., 22, 1859–1862 (1981); M. D. Matteucci and M. H. Caruthers, Tetrahedron Lett., 21, 719–722 (1980); and, M. D. Matteucci and M. H. Caruthers, J. Am. Chem. Soc., 103, 3185–3191 (1981).

Triester phosphate modified forms, in which X is a lower alkoxy group, can be obtained by ordinary methods, such as treatment of an oligonucleotide obtained by chemical synthesis with a tosylchloride solution of DMF, methanol and 2,6-lutidine (Moody H. M., et al., Nucleic Acids Res., 17, 4769–4782 (1989).

Alkylphosphonate modified forms, in which X is an alkyl group, can be obtained by ordinary methods using, for example, phosphoamidite (M. A. Dorman, et al., Tetrahedron, 40, 95–102 (1984); and, K. L. Agarwal and F. Riftina, Nucleic Acids Res., 6, 3009–3024 (1979)).

Phosphorothioate modified forms in which X is S can be obtained by ordinary methods such as solid phase synthesis using sulfur (C. A. Stein, et al., Nucleic Acids Res., 16, 3209–3221 (1988) or solid phase synthesis using tetraethylthiolam disulfide (H. Vu and B. L. Hirschbein, Tetrahedron Letters, 32, 3005–3008 (1991)).

Phosphorodithioate modified forms in which X and Y are both S can be obtained by, for example, solid phase synthesis by converting bis-amidite to thioamidite and allowing sulfur to act on the thioamidite (W. K. D. Brill, et al., J. Am. Chem. Soc., 111, 2321–2322 (1989)).

Phosphoroamidate modified forms in which X is a primary amine or secondary amine can be obtained by, for example, solid phase synthesis by treating hydrogen phosphonate with a primary or secondary amine (B. Froehler, et al., Nucleic Acids Res., 16, 4831–4839 (1988)), or by oxidizing amidite with tert-butyl hydroperoxide (H. Ozaki, et al., Tetrahedron Lett., 30, 5899–5902 (1989)).

Although synthesis of antisense oligoribonucleotide in which Z is a hydroxyl group is extremely difficult in comparison with synthesis of antisense oligodeoxyribonucleotide since the 2'-hydroxyl group on ribose (sugar) must be protected, it can be synthesized by suitably selecting the protecting group and phosphorylation method (see, Basic Microbiology Course, Vol. 8, Genetic Engineering, E. Ohtsuka, K. Miura, ed. T. Ando and K. Sakaguchi, Oct. 10, 1987, Kyoritsu Publishing Co., Ltd.).

Purification and confirmation of purity can be performed by high-performance liquid chromatography and polyacrylamide gel electrophoresis. Confirmation of molecular weight can be performed by Electrospray Ionization Mass Spectrometry or Fast Atom Bombardment-Mass Spectrometry.

The antisense oligonucleotide derivatives of the present invention acts at any stage from genomic DNA to mature mRNA, and suppression of its expression is thought to inhibit growth of leukemia cells. Thus, the antisense oligonucleotides of the invention of the present application is expected to be effective in the treatment of leukemia.

Moreover, as will be described later, the antisense oligonucleotide derivatives of the present invention is thought to specifically inhibit leukemia cells without inhibiting the growth of normal bone marrow cells. Thus, it can also be applied to "autologous bone marrow transplantation" and "autologous peripheral blood stem cell transplantation" in which, for example, after first removing bone marrow cells or peripheral blood stem cells from the body and treating them in vitro with the antisense oligonucleotide derivatives of the present invention to inhibit the growth of leukemia cells, only normal bone marrow cells or normal peripheral blood stem cells are returned to the body.

The antisense oligonucleotide derivatives of the present invention can also be used in the form of an external preparation such as a liniment or poultice by mixing with a suitable inactive base.

In addition, the antisense oligonucleotide derivatives of the present invention can also be used in the form of tablets, powders, granules, capsules, liposome capsules, injection preparations, liquids or nose drops by adding a vehicle, isotonic agent, solubility assistant, stabilizer, preservative or analgesic and so forth as necessary, or can be made into a freeze-dried preparation. These formulations can be prepared in accordance with routine methods.

The antisense oligonucleotide derivatives of the present invention can be applied directly to the affected area of the patients, or applied so as to be able to reach the affected area as a result of intravascular administration and so forth. Moreover, antisense inclusion materials can also be used to improve duration and membrane permeation. Examples of these include liposomes, poly-L-lysine, lipids, cholesterol lipofectin and their derivatives.

The dose of the antisense oligonucleotide derivative of the present invention is such that a preferable amount can be used by suitably preparing a dose according to the patient's condition, age, sex and body weight. In addition, the administration method can be suitably selected from various administration methods, including oral administration, intramuscular administration, intraperitoneal administration, intradermal administration, subcutaneous administration, intravenous administration, intraarterial administration and rectal administration according to the patient's conditions, the drug forms and so forth.

The following provides a detailed explanation of the present invention through Examples.

EXAMPLES

Synthesis Example 1

The oligodeoxyribonucleotides used below (SEQ ID NOS: 1 to 8) were synthesized using an automatic synthesizer (Applied Biosystems), purified by high-performance liquid chromatography, precipitated three times with ethanol, and suspended in phosphate buffer. The synthesized oligonucleotides were as listed below.

SEQ ID NO: 1: Sense sequence of transcription capping site (SE1)

SEQ ID NO: 2: Antisense sequence of transcription capping site (AS1)

SEQ ID NO: 3: Sense sequence of transcription capping region (SE2)

SEQ ID NO: 4: Antisense sequence of transcription capping region (AS2)

SEQ ID NO: 5: Sense sequence of translation starting region (SE3)

SEQ ID NO: 6: Antisense sequence of translation starting region (AS3)

SEQ ID NO: 7: Sense sequence of exon 6 (SE4)

SEQ ID NO: 8: Antisense sequence of exon 6 (AS4)

Example 1

$5 \times 10^4$ cells/ml of leukemia cell line K562 positive for WT1 expression were inoculated into RPMI 1640 medium not containing fetal calf serum (FCS) contained in the wells of a flat-bottom 96-well plate in the amount of 100 $\mu$l/well. Each oligonucleotide was added to a series of three wells to a final concentration of 200 $\mu$g/well. After incubating for 2 hours, FCS was added to each well to a final concentration of 10%. Oligonucleotides were then added to the culture in an amount equal to half the above-mentioned amount every 24 hours.

After culturing for 96 hours, the numbers of viable cells were counted using the pigment elimination method. An equal volume of PBS not containing nucleotide was added as the control culture, and the number of cells of this control culture was taken to be 100%.

The results are shown in FIG. 1. As is clear from this figure, all of the antisense oligonucleotides powerfully inhibited cell growth in comparison with the corresponding sense oligonucleotides.

Example 2

Figure 2:
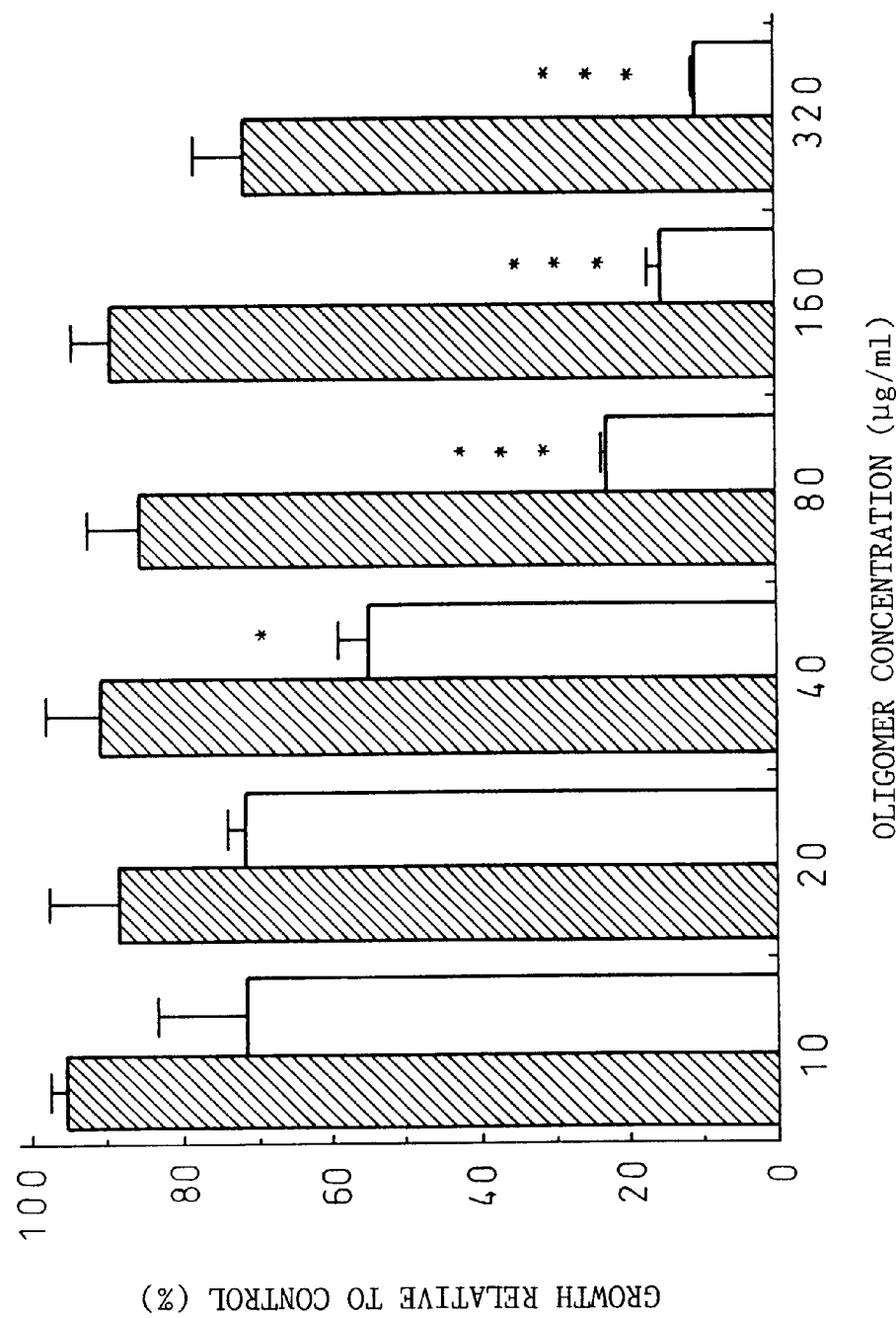
FIG. 2 is a graph showing the relationship between the concentrations of oligonucleotides SE3 and AS3 and the growth of leukemia cell line K562.

The same experiment as that described in Example 1 was performed, but oligonucleotides SE3 and AS3 were added at various concentrations. As is clear from FIG. 2, although sense oligonucleotide (SE3) virtually did not inhibit cell growth, antisense oligonucleotide (AS3) inhibited cell growth in a dose dependent manner.

Example 3

Figure 3:
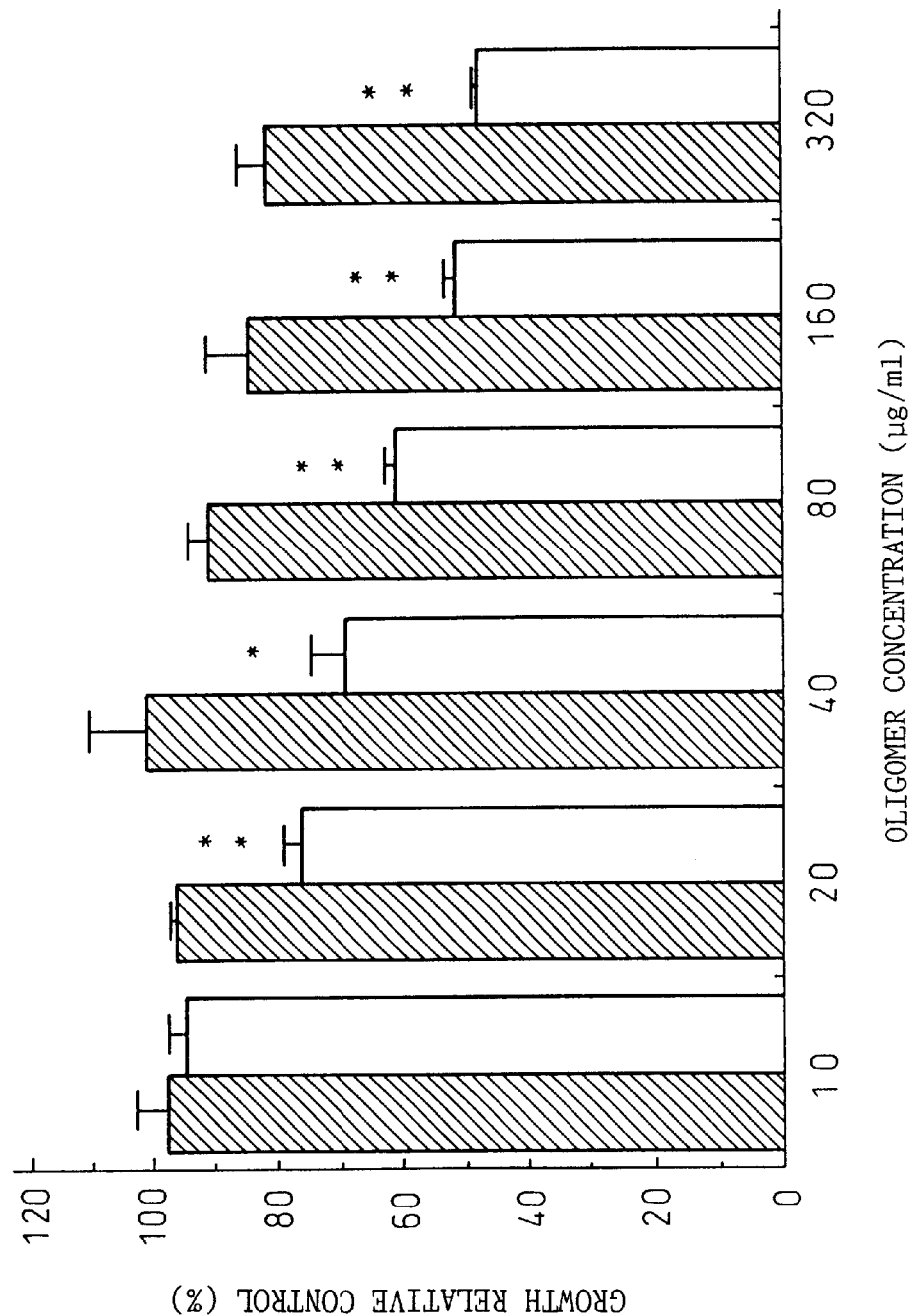
FIG. 3 is a graph showing the relationship between the concentrations of oligonucleotides SE4 and AS4 and the growth of leukemia cell line K562.

The same experiment as that described in Example 1 was performed, but oligonucleotides SE4 and AS4 were added at various concentrations. As is clear from FIG. 3, although sense oligonucleotide (SE4) virtually did not inhibit cell growth, antisense oligonucleotide (AS4) inhibited cell growth in a dose dependent manner.

Example 4

Figure 4:
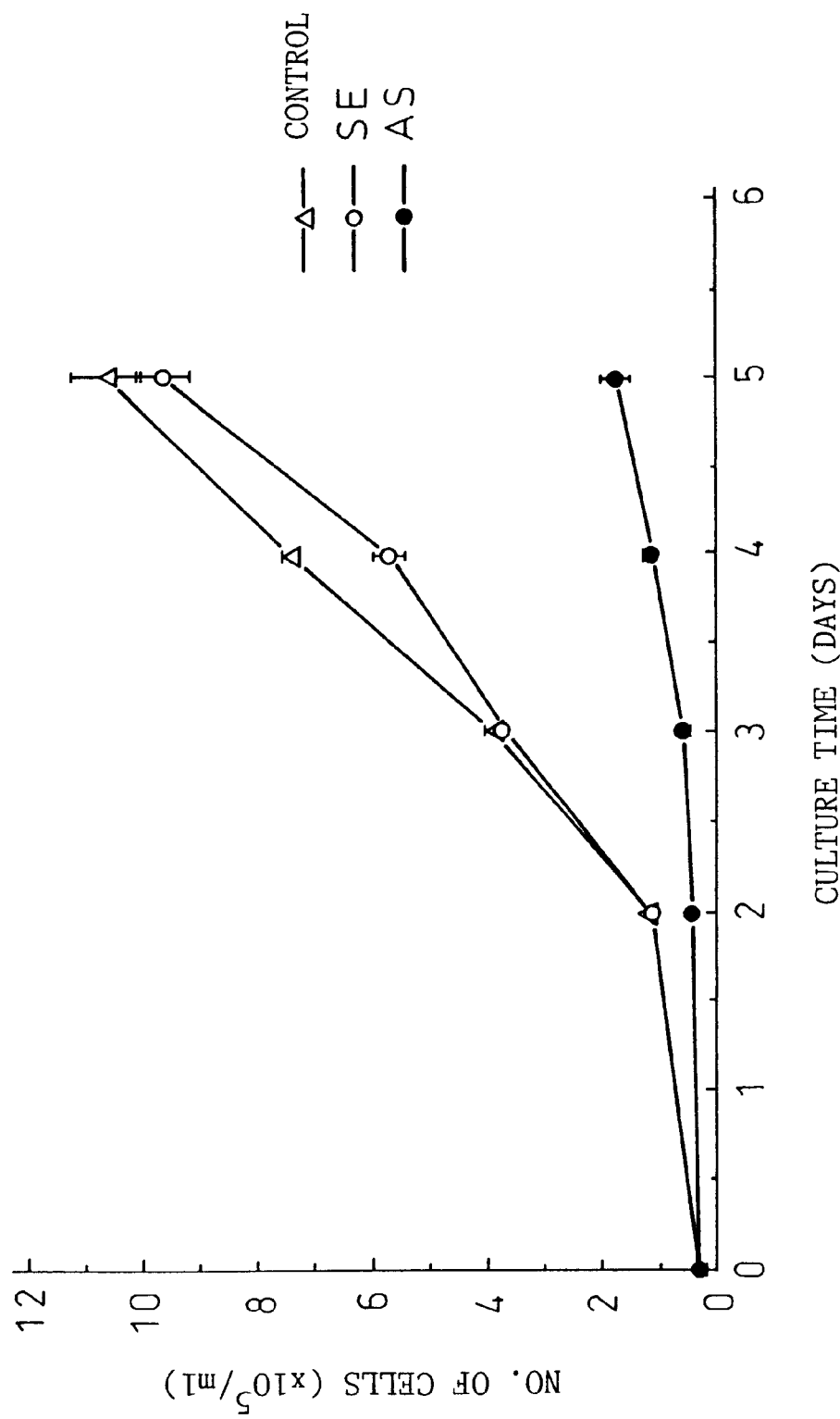
FIG. 4 is a graph showing the time-based effects of oligonucleotides SE3 and AS3 on the growth of leukemia cell line K562.

The same experiment as described in Example 1 was performed. However, the cells were cultured in a flat-bottom 24-well plate at a concentration of $5 \times 10^4$ cells/ml and in the amount of 1 ml/well. Oligonucleotides SE3 and AS3 were added and the numbers of viable cells were counted daily for 2 to 5 days. The results are shown in FIG. 4. As is clear from the figure, although cell growth similar to the control was observed in the case of adding sense oligonucleotide, in the case of adding antisense oligonucleotide, cell growth was inhibited.

Example 5

Figure 5:
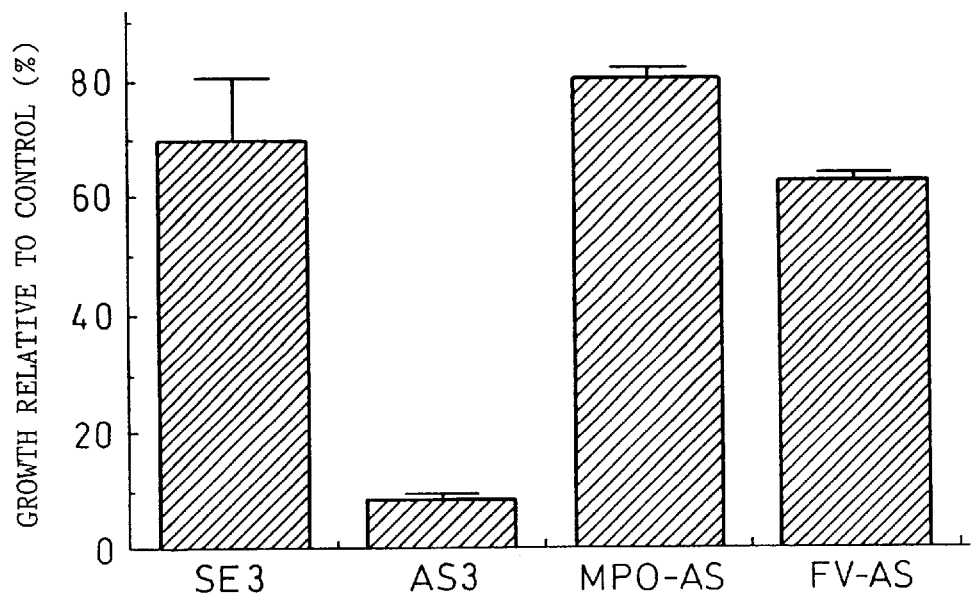
FIG. 5 is a graph showing the effects of various oligonucleotides on the growth of leukemia cell line K562.

The same experiment as described in Example 1 was performed. However, SE3, AS3, an antisense oligonucleotide 5'-AGAGAAGAAGGGAACCCC-3' (SEQ ID NO: 20) (MPO-AS) to myeloperoxidase (MPO) gene, and an antisense oligonucleotide 5'-GCGTGGGCAGCCTGGGAA-3' (SEQ ID NO: 21) (FV-AS) to blood coagulation factor V (FV) were used for the oligonucleotides. As is clear from FIG. 5, cell growth was inhibited only in the case of using AS3.

Example 6

Figure 6:
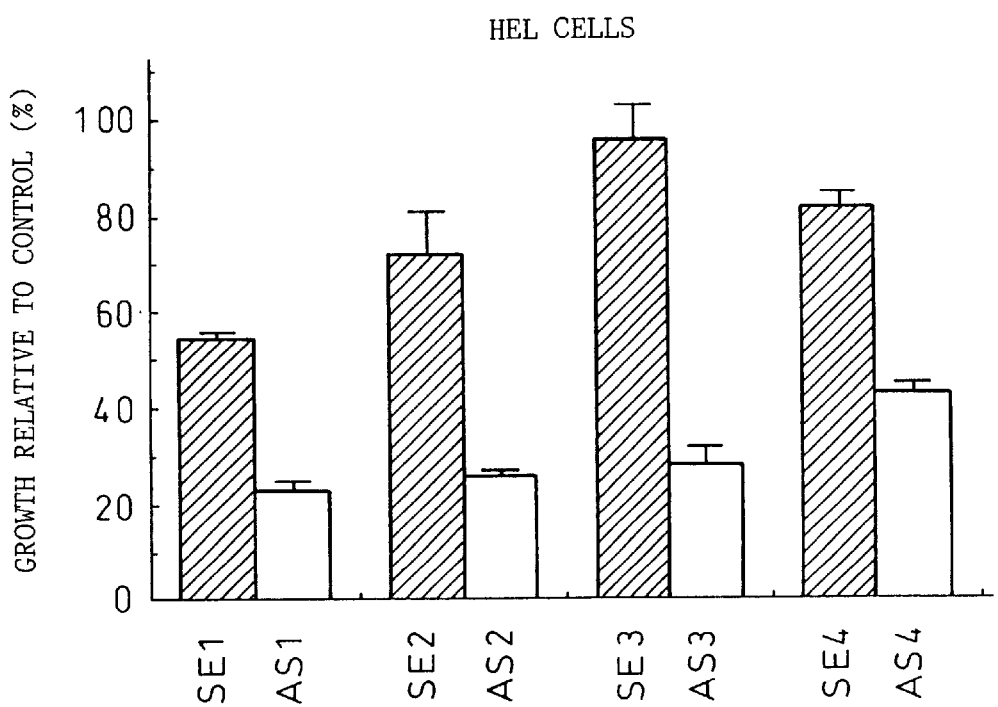
FIG. 6 is a graph showing the inhibitory effects of various oligonucleotides on the growth of leukemia cell line HEL positive for expression of WT1.
Figure 7:
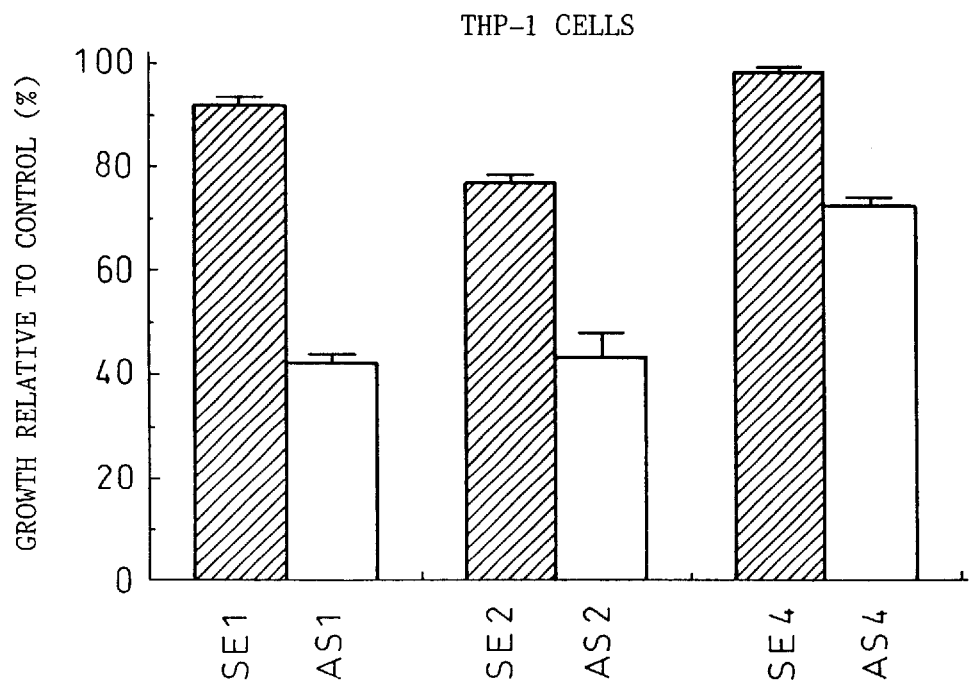
FIG. 7 is a graph showing the inhibitory effects of various oligonucleotides on the growth of leukemia cell line THP-1 positive for expression of WT1.
Figure 8:
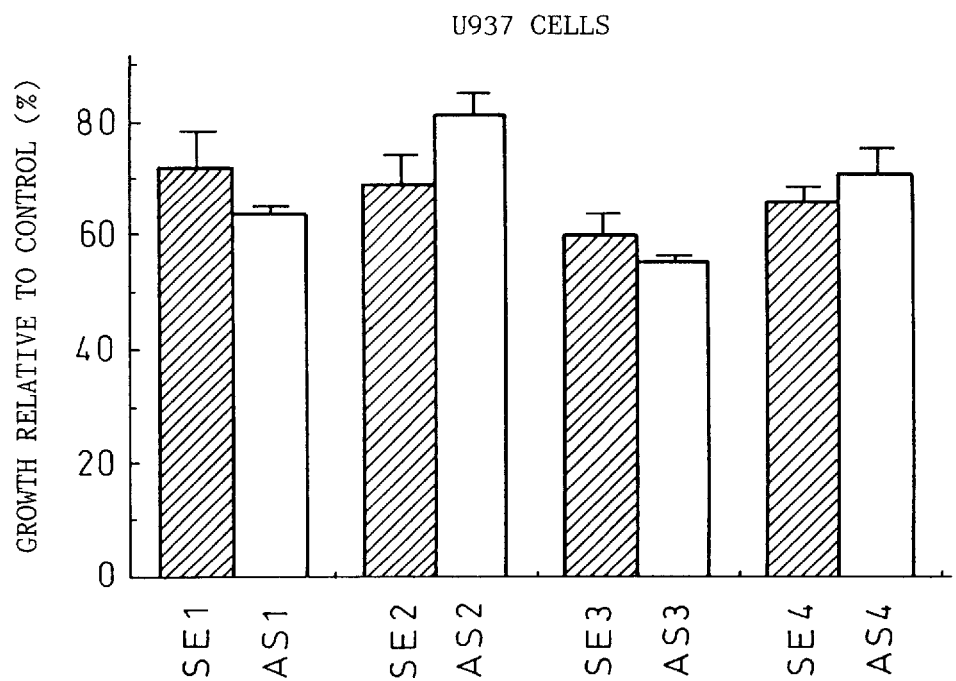
FIG. 8 is a graph showing the inhibitory effects of various nucleotides on the growth of malignant lymphoma cell line U937 negative for expression of WT1.

The same experiment as described in Example 1 was performed, but WT1 expression-positive cell lines HEL and THP-1 as well as WT1 expression-negative cell line U937 were used as the experimental cells. The same eight types of oligonucleotides used in Example 1 were used as the oligonucleotides. In the case of using WT1 expression-positive cell line HEL (FIG. 6) or THP-1 (FIG. 7), cell growth was inhibited by antisense oligonucleotide. In contrast, in the case of using WT1 expression-negative cell line U937 (FIG. 8), cell growth was not inhibited even if antisense oligonucleotide was added.

Example 7

Bone marrow cells from leukemia patients and healthy volunteers were treated with heparin and suspended in RPMI 1640 medium to obtain bone marrow mononuclear cells by Ficoll-Hypaque density gradient centrifugation. A protein (100 μl/well) of the above-mentioned mononuclear cells at a cell density of $1.5 \times 10^6$ cells/ml were added to a flat-bottom 96-well plate containing A-MEM containing GM-CSF (100 ng/ml) and IL-3 (100 units/ml). Treatment with oligonucleotides (SE3 and AS3) was performed in the same manner as Example 1.

After 96 hours, the cells were collected and plated in methylcellulose medium [1.2% methylcellulose α-MEM, 20% FCS, GM-CSF (100 ng/ml), G-CSF (100 ng/ml), IL-3 (100 units/ml) and SCF (10 ng/ml)]. Culturing was performed in three series. The number of leukemia cell colonies (CFU-L) and granulocytic macrophage colonies (CFU-GM) were counted on day 14.

Figure 9:
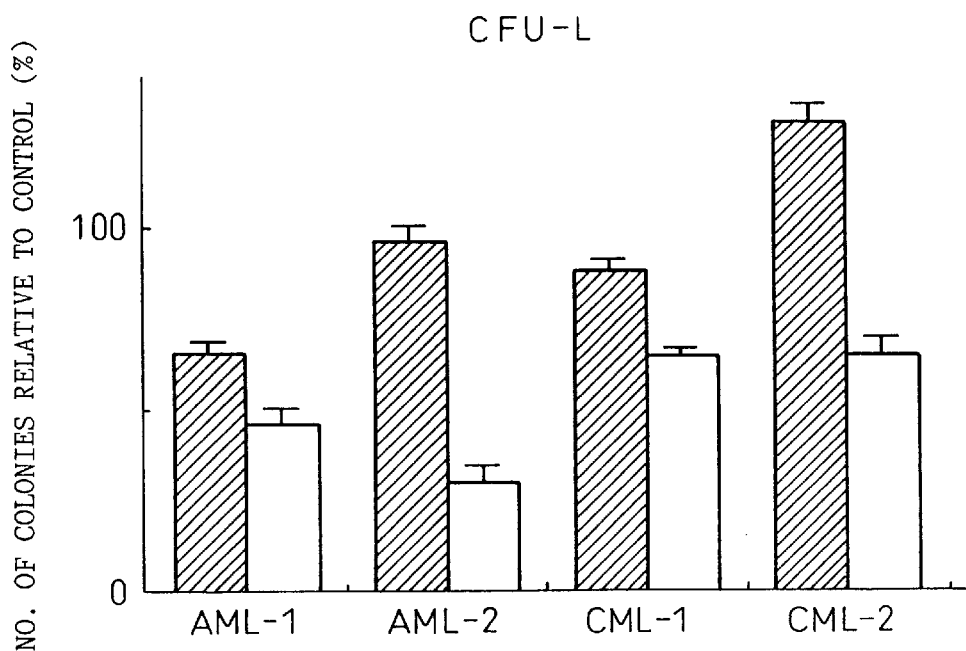
FIG. 9 is a graph showing the effects of oligonucleotides SE3 and AS3 on the formation of leukemia cell colonies from bone marrow mononuclear cells derived from leukemia patients.
Figure 10:
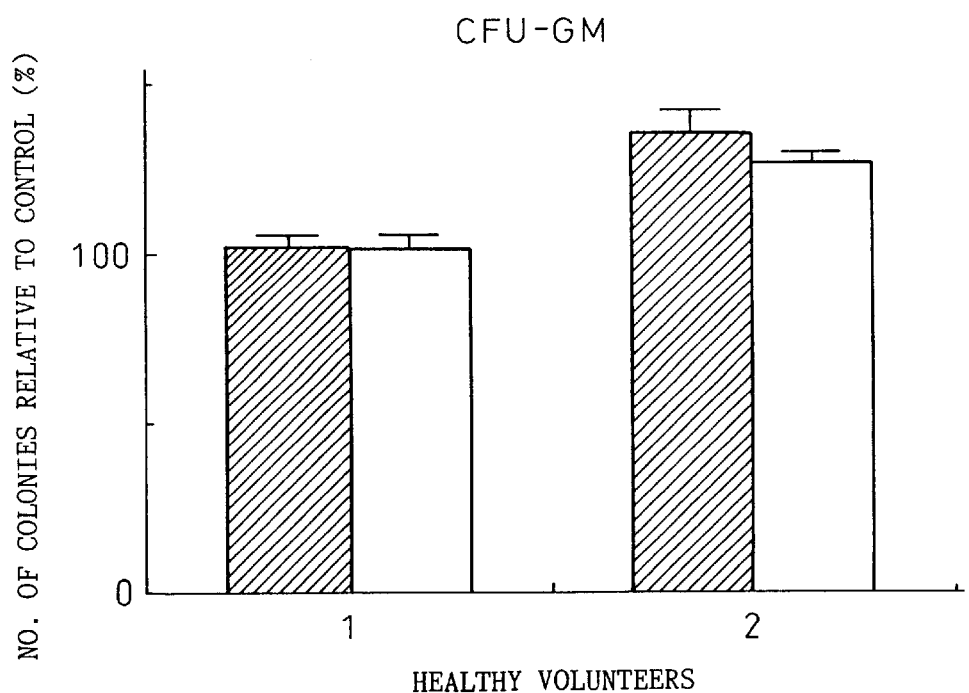
FIG. 10 is a graph showing the effects of oligonucleotides SE3 and AS3 on the formation of granulocytic macrophage colonies from bone marrow mononuclear cells derived from healthy volunteers.

FIG. 9 shows the morphology of the leukemia colonies in samples from four leukemia patients (two acute myeloid leukemia (AML) patients and 2 chronic myeloid leukemia (CML) patients). The formation of colonies can be seen to be inhibited by antisense oligonucleotide. FIG. 10 shows the appearance of granulocytic macrophage colonies in samples from healthy volunteers. Colony formation is not inhibited by either of the antisense oligonucleotides.

Example 8

Random oligonucleotide, oligonucleotide AS1, oligonucleotide AS2 or oligonucleotide AS3 was added at a concentration of 200 μg/ml to K562 cells (A) or fresh leukemia cells from a patient with AML (B) at a cell density of $5 \times 10^4$ cells/well in a 24-well plate, followed by addition of the oligonucleotides at a concentration of 100 μg/ml every 24 hours. The cells were harvested 4 days after the initial treatment with oligonucleotide, washed with PBS and lysed with Laemli sample buffer.

Each cell lysate from $2 \times 10^4$ cells was boiled for 5 minutes, and then applied to each lane of 5% dodecylsodium sulfate-polyacrylamide gel. Following electrophoresis, the proteins were transferred to an Immobilon polyvinylidene difluoride filter (Millipore Corp. Massachusetts, USA). This filter was then probed using an anti-WT1 polyclonal antibody to synthetic polypeptide (amino acid positions 177 to 192: Lys His Glu Asp Pro Met Gly Gln Gln Gly Ser Leu Gly Glu Gln Gln (SEQ ID NO: 22)). This was followed by treatment with horseradish peroxidase-bound anti-immunoglobulin antibody (Amersham, Little Chalfont, U.K.). After washing, the filter was immersed in detection reagent (Amersham, Little Chalfont, U.K.) for 1 hour followed by autoradiography treatment for 1 to 5 minutes.

After washing twice with TBST (Tris buffer containing 0.05% Tween 20), the filter was probed with anti-actin monoclonal antibody (Oncogene Science Inc., New York, USA) followed by autoradiography in the manner described above.

The density of the bands corresponding to WT1 protein and actin were measured with a CS-9000 densitometer (Shimizu, Kyoto) followed by calculation of the WT1/actin ratio.

Figure 11:
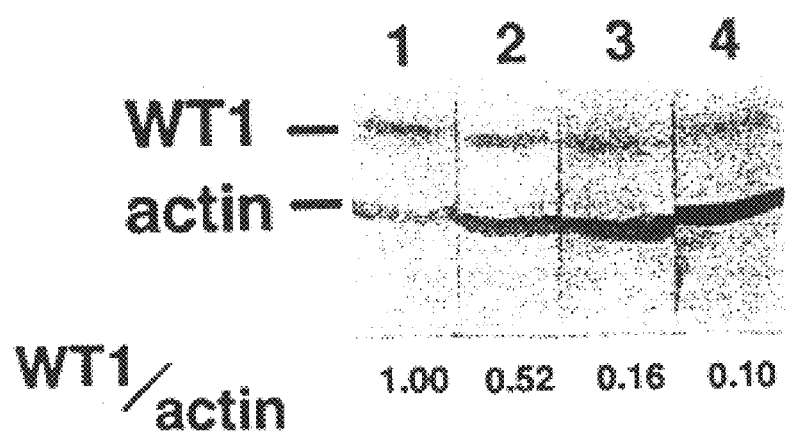
FIGS. 11A–11B, panel 11A is a photograph of the results of electrophoresis indicating a decrease in the level of WT1 protein in cells in the case of adding various WT1 antisense oligonucleotides to a culture of K562 cells; panel 11B indicates a decrease in the level of WT1 protein in cells in the case of adding WT1 antisense oligonucleotides to fresh leukemia cells from a patient with AML.
Figure 11:
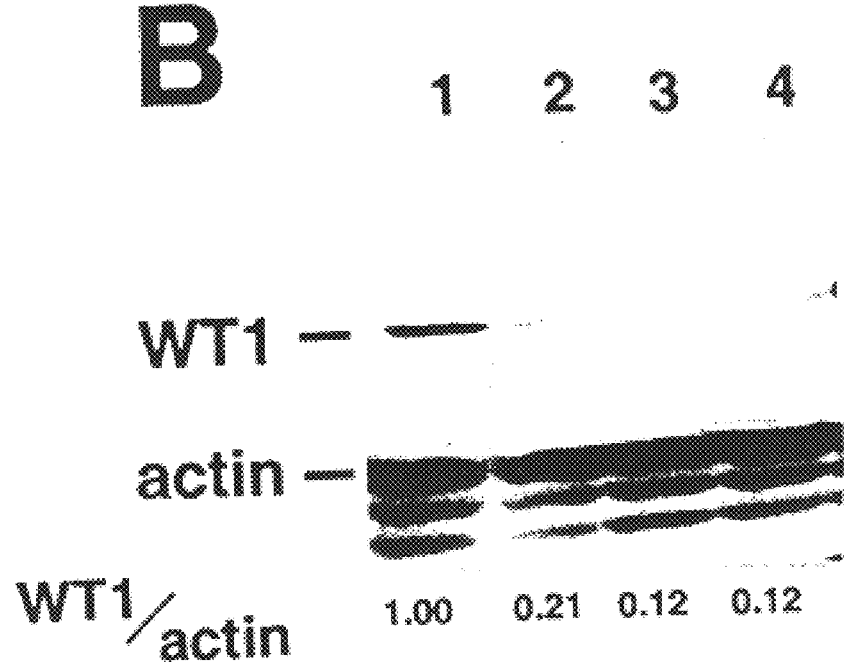

The results are shown in FIGS. 11A and B. In these figures, lane 1 shows the results in the case of adding random oligonucleotide, lane 2 the case of adding oligonucleotide AS3, lane 3 the case of adding oligonucleotide AS1, and lane 4 the case of adding oligonucleotide AS2. In these figures, A indicates the results in the case of using K562 cells, while B indicates those in the case of using fresh leukemia cells from a patient with AML.

As is clear from FIG. 11A, in the case of adding WT1 oligonucleotide to medium containing K562 cells, the level of WT1 protein decreased significantly. On the other hand, control in the form of random nucleotide did not affect the level of WT1 protein. In addition, as is clear from FIG. 11B, in the case of adding WT1 oligonucleotide to medium containing leukemia cells recently isolated from a patient with AML, the level of WT1 protein decreased significantly. These results clearly showed that WT1 antisense oligonucleotide specifically inhibits the growth of leukemia cells by decreasing the level of WT1 protein.

Industrial Applicability

As has been stated above, the antisense oligonucleotides of the present invention is effective in inhibiting the growth of leukemia cells, and is therefore expected to be useful as a novel leukemia treatment.

What is claimed is:

1. A method for treating leukemia comprising, administering ex vivo an antisense oligonucleotide against Wilms' tumor gene, wherein the antisense oligonucleotide is 9–30 nucleotides in length and comprises all or a part of SEQ ID NO: 2, 4, 6 or 8.

2. A method as set forth in claim 1, wherein said antisense oligonucleotide is an antisense oligonucleotide to at least nine continuing nucleotides at the transcription capping site of the Wilms' tumor gene.

3. A method as set forth in claim 1, wherein said antisense oligonucleotide is an antisense oligonucleotide to at least nine continuing nucleotides including the translation starting region of the Wilms' tumor gene.

4. A method as set forth in claim 1, wherein said antisense oligonucleotide is an antisense oligonucleotide corresponding to at least nine continuing nucleotides in an exon of the Wilms' tumor gene.

* * * * *

UNITED STATES PATENT AND TRADEMARK OFFICE
CERTIFICATE OF CORRECTION

PATENT NO. : 6,277,832 B1
DATED : August 21, 2001
INVENTOR(S) : Sugiyama et al.

It is certified that error appears in the above-identified patent and that said Letters Patent is hereby corrected as shown below:

<u>Title page,</u>
Item [73], Assignee, should read:
-- Tadamitsu Kishimoto, Tondabayashi-shi;
   Haruo Sugiyama, Mino-shi; both of (JP) --.

Signed and Sealed this

Eleventh Day of April, 2006

JON W. DUDAS
*Director of the United States Patent and Trademark Office*